United States Patent
Reckhaus

(10) Patent No.: US 9,635,840 B2
(45) Date of Patent: May 2, 2017

(54) METHOD AND APPARATUS FOR SUPPORTING THE PRESERVATION OF THE INSECT POPULATION

(71) Applicant: RECKHAUS AG, Gais (CH)

(72) Inventor: Hans-Dietrich Reckhaus, Teufen (CH)

(73) Assignee: RECKHAUS AG, Gais (CH)

( * ) Notice: Subject to any disclaimer, the term of this patent is extended or adjusted under 35 U.S.C. 154(b) by 0 days.

(21) Appl. No.: 14/409,046

(22) PCT Filed: Aug. 22, 2013

(86) PCT No.: PCT/EP2013/002527
§ 371 (c)(1),
(2) Date: Dec. 18, 2014

(87) PCT Pub. No.: WO2014/029503
PCT Pub. Date: Feb. 27, 2014

(65) Prior Publication Data
US 2015/0359208 A1    Dec. 17, 2015

(30) Foreign Application Priority Data

Aug. 24, 2012 (DE) .......... 10 2012 016 885
Oct. 24, 2012 (DE) .......... 10 2012 020 912

(51) Int. Cl.
*A01K 67/033* (2006.01)
*G01N 33/50* (2006.01)

(52) U.S. Cl.
CPC ....... *A01K 67/033* (2013.01); *G01N 33/5085* (2013.01); *G01N 2333/43552* (2013.01)

(58) Field of Classification Search
CPC .. A01K 67/033; A01K 67/00; G01N 33/5085; G01N 2333/43552
USPC ........................................... 119/6.5
See application file for complete search history.

(56) References Cited

U.S. PATENT DOCUMENTS 6,129,935 A * 10/2000 White ............... A23K 1/1873
                                                119/6.5
6,274,137 B1 * 8/2001 Mensah ............. A01N 63/04
                                                424/115
6,440,406 B1 * 8/2002 Lopez, Jr. .......... A01N 37/40
                                                424/405

(Continued)

OTHER PUBLICATIONS

International Preliminary Report on Patentability, Issued Feb. 24, 2015 (Feb. 24, 2015).

(Continued)

*Primary Examiner* — Patrick Hawn
(74) *Attorney, Agent, or Firm* — Benesch, Friedlander, Coplan & Aronoff LLP

(57) ABSTRACT

Method for supporting the preservation of the insect population, having the following steps of: determining the lethal effect of a product unit on an insect population, determining a difference in the insect population on the basis of the effect of a particular quantity of product units, determining the actual insect population in a predetermined area, determining a desired insect population in the predetermined area, which desired insect population is derived from the actual insect population in the predetermined area and the difference in the insect population, and creating a basis of life for the desired insect population in the predetermined area by adapting the biological nature of the predetermined area.

9 Claims, 2 Drawing Sheets

(56) References Cited

U.S. PATENT DOCUMENTS

Figure 1:
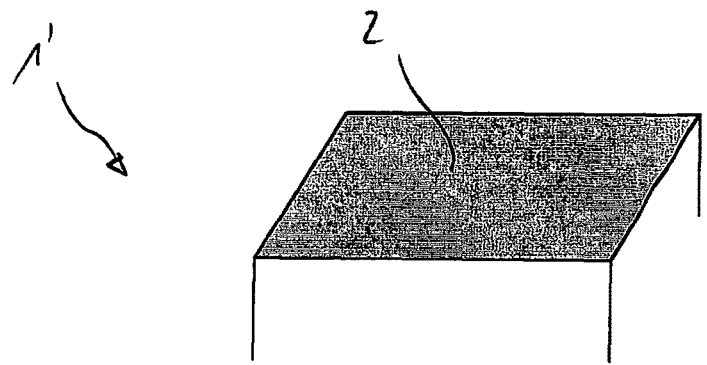
Figure 1:
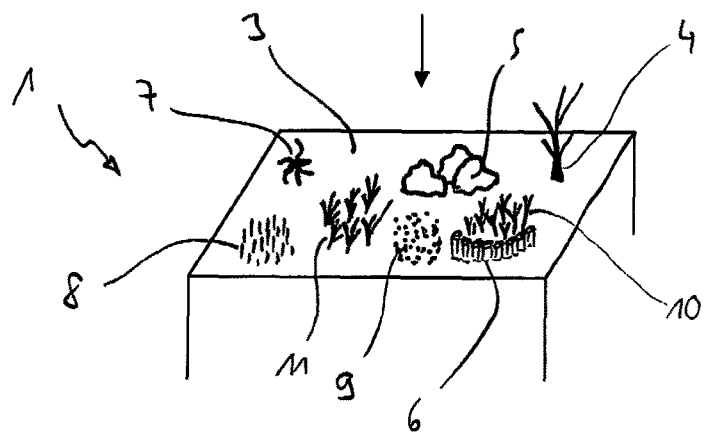

| | | | | |
|---|---|---|---|---|
| 6,544,513 | B2* | 4/2003 | Mensah | A01N 63/04 424/115 |
| 6,557,487 | B1* | 5/2003 | Fleischmann | A61K 35/64 119/6.5 |
| 8,994,529 | B2* | 3/2015 | White | A01M 1/2022 239/329 |
| 2003/0172875 | A1* | 9/2003 | Fleischmann | A61K 35/64 119/6.5 |
| 2007/0169401 | A1* | 7/2007 | Chyun | A01M 1/145 43/113 |
| 2010/0312403 | A1* | 12/2010 | White | A01M 1/2022 700/283 |
| 2013/0039863 | A1* | 2/2013 | Yee | A01N 65/00 424/45 |
| 2015/0216158 | A1* | 8/2015 | Mizrach | A01M 1/2016 43/107 |

OTHER PUBLICATIONS

International Search Report PCT/EP2013/002527.
Caio Fabio Stoffel Efrom, Luiza Rodrigues Redaelli, Rafael Narciso Meirelles and Claudia Bernardes Ourique; Side-Effects of Pesticides Used in the Organic System of Production on Apis mellifera Linnaeus, 1758; Brazilian Archives of Biology and Technology, vol. 56, n. 1: pp. 47-53, Jan.-Feb. 2012; ISSN 1516-8913.
Curtis Petzoldt, Joseph Kovach and James Engel; Evaluating Pesticides for Their Impact on Beneficial Organisms; 1 IPM Program, New York State Agricultural Experiment Station, 630 W. North Street, Geneva, New York 14456, 2 Department of Entomology, OARDC. Wooster, Ohio 44691.
Insect Respect; c/o Reckhaus AG, Bundstrasse 11, CH-9053 Teufen; Sep. 27, 2013.
S.A. Hassan; Standard methods to test the side-effects of pesticides on natural enemies of insects and mites; International Organization for Biological Control of Noxious Animals and Plants, West Palaearctic Regional Section; Bulletin OEPP/EPPO Bulletin 15, 214-255 (1985).
Office Action in Chinese Patent Application No. 201380044021.7 dated Oct. 23, 2015.
Ming Guangzeng et al., "Experiments of influence of several pesticides to main natural enemies of pests of pear trees", Hebei Fruit Tree, No. 2, 2005, pp. 9, 12, 2005.
Wei Yongping et al., "sustainable control effect on apple orchard pests by habitat adjustment", Plant Conservation Science, vol. 20, No. 1, pp. 204-206, Feb. 2004.

* cited by examiner

METHOD AND APPARATUS FOR SUPPORTING THE PRESERVATION OF THE INSECT POPULATION

The present invention relates to a method for supporting the preservation of a population of insects.

In many residential and commercial areas products are used for the control of insects. Due to this, many insects and other arthropods are killed and then missing in the ecosystem.

The insects and the other arthropods are also killed by other products and therefore removed from the ecosystem. These are, for example, products, which during their application unintentionally harm the insects, particularly as a result of a collision with moving products, particularly those products that mainly serve for the transport of persons or goods. As another example of products that unintentionally harm the insects during their application, headlights are mentioned, which attract the insects by their light and which burn them at a too close contact.

As a result of these intentional or unintentional effects of the products, the insects are missing which in particular pollinate the flowers and serve as food for birds, fish, reptiles and mammals.

Therefore, the object of the present invention is to compensate for these losses of the insects.

This object is solved by the teachings according to the independent claims. Preferred embodiments of the invention are the subject matters of the dependent claims.

For the method for supporting the preservation of the population of insects according to the present invention: at first, it is determined the lethal effect of a product unit on the population of insects and it is determined the difference of the population of insects due to the effects of a predetermined amount of the product units.

Then, the actual population of insects on a predetermined area is determined, and a target population of insects on said predetermined area is determined, wherein the target population of insects is derived from the actual population of insects on the predetermined area and the difference of the population of insects.

For the target population of insects, then a livelihood on the predetermined area is created by adjusting the biological properties of the predetermined area.

A variety of products have deadly, also lethal effect on the population of insects. For example, by products for insect control, the insects and the other arthropods such as spiders are removed and they are also usually killed by these products from an area, where the insects and the arthropods are undesirable, for example, for reasons of hygiene. Such products for insect control usually have a degree of lethal effect, meaning a certain potential for killing a given amount of insects, which is characteristic for this product. This potential of the product unit of a product for insect control corresponds to its lethal effect on the population of insects. Preferably, in determining the lethal effect of a product, also the period of time is considered, in which the product is applied to or it is taking effect. Depending on the products, for the determination of its lethal effect are also taking into consideration, preferably the instant of time (season, during daytime, during nighttime, and so on) and/or the environment (buildings, outdoors, and so on), in which the product unit is applied to.

Also moving products, such as those acting for the transport of persons or goods, in particular such as motor vehicles, trains, barges, aircraft taking off or landing or gondolas to mountain railways and other rides or alternatively powered vehicles such as bicycles have lethal effects on the population of insects. If these products are moving with particular higher speeds, they frequently collide and in large quantities with the insects and the other arthropods, especially with the front ends of these products, the insects and the other arthropods being mostly killed. Consequently, such products also have a certain degree of a lethal effect, meaning a certain potential for killing a certain amount of insects. Also for determining the lethal effect of such moving products, in addition to the operating effects, are preferably considered the period of time of the application, the instant of time of the application and the field of the application. The proportions of the killed insect species depend on the population of insects in the area, in which such a product is moved. The potential of the product unit to kill a certain amount of these insects corresponds to the lethal effect on the population of insects.

Also many other products which have particularly fast moving parts, such as wind turbines have a lethal effect on the population of insects, their blades colliding with the insects. Similarly, many products having moving parts for a wide variety of purposes are deadly traps for insects. For example, rotary mowers, which are used for forage harvest, are so powerful that due to the high working speed also larger insects such as bees or butterflies can not leave the harvest area on time and suffocate in the forage.

A variety of other products have in addition to the desired product effect also an undesired lethal effect on the population of insects. For example, the light of headlamps, in particular of high-performance lighting equipment such as floodlights in sports stadiums and airports or even the light from street lighting are attracting many insects which are killed in close contact with these lighting systems, in particular by their heat effects.

Therefore, the in preceding sections mentioned examples as well as a variety of other products, whose application harm the insects or the other arthropods, have some potential to kill a certain amount of insects. The potential of a product unit corresponds to its lethal effect on the population of insects. For the determining the lethal effect of a product unit, for simplifying the application of this method, preferably average values are used for the product or a similar product, wherein the differences in the lethal effects such as a larger or a smaller frontal area of a vehicle are preferably taken into account by correction factors.

Because of this lethal effect of the use or the application of a predetermined amount of the product units, the resulting difference of the population of insects can be determined.

Thus, for example, a product unit of an adhesive insect trap having about 100 $cm^2$ adhesive surface catches in average 150 flies weighing about 720 mg. For example, 100,000 cans of bug spray (400 ml) kill in average about 50 kg of insects, so that the difference of the population of insects for 100,000 doses of an insecticide spray is about 50 kg of insects.

Frequently, particular products for insect control exert their lethal effect mainly on such species of insects, which are less important for to ecosystem and therefore less valuable, such as houseflies.

For a product unit of a passenger car with a frontal area of about 2 $m^2$, for example, in average over the seasons, with an average annual mileage of 18,000 km, more than 30 g of insects are killed per year. The difference of the population of insects due to the effect of the moving products is therefore particularly affected by the flow against area, the movement distance and the movement speed as well as by the density of the population of insects in the area, in which the products are moving.

Each area, in particular outside of buildings, is naturally occupied by a certain amount of typically several types of insects, and thus has an actual population of insects. For carrying out the method according to the present invention for supporting the preservation of the population of insects, the actual population of insects will be determined on a predetermined area. In particular, the actual population of insects can be determined on an area due to the biological properties, which are also referred to as a quality value. The same or at least similar biological properties are the basis of empirical values for areas having estimated the size of the population of insects due to the different frequency of certain types of the insects or the other arthropods per square meter per year. Again, an adaptation of the determined value is possible by using characteristic numbers.

Starting from the actual population of insects on an area, a target population of insects of this predetermined area is determined in connection with the difference of the population of insects resulting from the effects of a predetermined amount of product units and the target population of insects for the area which support the preservation of the population of insects. Thereby, the target population of insects may be the sum of the actual population of insects and the difference of the population of insects. Furthermore, the target population of insects can be determined by a sum of the actual population of insects and the difference of the population of insects, which is increased or decreased by a factor, or by any other appropriate calculation or other determination methods such as using tables with empirical determined values. Conventionally, for such calculations, the body weight of the insects in milligrams per square meter of the area is used as the unit of the population of insects.

For such calculations, preferably, also correction factor can be incorporated to take into account for any environmental value of the biodiversity. When using such a correction factor, then a higher value of the correction factor could be assigned to particularly valuable or useful insects and thus a higher compensation value can be assigned compared to species of insects which are judged less valuable for the biodiversity of the ecosystem. Thus, for example, higher correction factors for the biodiversity are assigned to bees or ants compared to, for example, house flies or fruit flies.

Thus, for the predetermined area forming the livelihood for the target population of insects, this area must have at least predetermined biological properties, meaning having a quality value. Therefore, the biological properties of the area are adapted in a further step of the method so that it provides a livelihood for the determined target population of insects on this predetermined area. Thereby, the quality value of the biological properties is changed so that on this area is created a livelihood for a larger population of insects, the target population of insects. This then results in a settlement of an additional mass of insects, so that the predetermined area has the determined target population of insects. Based on the difference of the population of insects due to the effects of a predetermined amount of product units, the preservation of the population of insects in the ecosystem is supported by this method.

The lethal effect of a product unit on the population of insects is preferably mechanically and/or chemically.

Under the mechanical product units to control insects fall in particular fly swatters or glue traps, wherein the glue traps have not only the mechanical retention effect, but also often chemical agents for a faster killing of the insects or for a attracting of the insects.

Under the mechanical product units fall in particular moving products such as single or dual motor vehicles, passenger or freight trains, aircrafts taking off or landing, river boats, gondolas for cable cars of other fairground rides, or alternatively powered vehicles such as bicycles.

As purely chemical product units should be understood the product units, which have their effect based on an active ingredient deployed in a room or on a surface, such as insect sprays. Preferably, in addition to mechanical and/or chemical agents, for special applications, biological agents are preferably used in conjunction with mechanical and or chemical agents.

In particular, the lethal effect of a preferred single product unit on the population of insects is determined due to the toxicity of the preferably chemical agent and the amount of the agent acting on the population of insects. The lethal effect is especially larger, the more effective is the agent, the higher is the concentration of the agent, and greater is amount of applied agent and of the released agent, respectively.

Also, the lethal effect of a preferred chemically and/or preferred mechanically acting product unit on the population of insects is determined by the properties of the area and/or by the geometry of the product unit. Product units with these features are in particular insect traps, into which insects are lured by the color or the smell of the product unit. There, for example, the insects fall into an inescapable trap, like a vessel with a liquid solution whose surface tension is reduced, an adhesive surface or a cavity, which insects can not leave.

The surface properties and/or the geometry are preferred factors for the lethal effect of a preferably mechanically acting moving product unit on the population of insects. In particular, the color of the surface of the moving product unit can cause insects to move to this product unit and thus into the path of movement of the product unit, in which they then collide with the moving product. Furthermore, the geometry is an important factor for the amount of the insects colliding with the product as the configuration of a closed surface or a perforated surface, like for example a fine mesh, and the size, in particular the surface of the end face of the moving product in particular due to the different properties of the air flow.

Furthermore, for a preferred embodiment of the method, product units are used whose lethal effect on the population of insects is determined due to a negative effect on the fertility of the insects. By such a product unit, the difference of the population of insects is caused in the way that due to the destroyed fertility of the insects, the difference of the population of insects is caused with a temporally offset after the application of the product unit.

For each of the aforementioned type of product units, the lethal effect on the population of insects may be reinforced by at least one attractant. The effect is amplified by the attractant in that the insects are attracted to the product unit, so that the product unit can act on a larger population of insects compared to the area in which the product unit is applied to or which the product unit affects.

In the case of a chemically active product unit, which affects a certain type or more types of insects, such an attractant can be in particular a scent. Especially, for moving product units, the color, in particular a brighter shade of yellow or lighting acts as an attractant for insects. This applies in particular to the headlamps of the moving product units, such as vehicles, or generally to all kinds of lighting devices.

For the moving product units, the lethal effect is determined in particular by the size of the flow against surface substantially perpendicular to the direction of movement and the length of the distance traveled by this product unit, in particular for a speed lying above a speed threshold. The speed threshold the moving product unit depends particularly also on its geometry. For a motor vehicle, it is about 50 km/h.

The lethal effect of such a product unit increases with larger values, in particular with larger values of the flow against surface, the distance traveled and the speed. Over the speed threshold, the insects in the air are essentially no longer guided around the flow against surface by the flow of the air around or collide on it gently without harm, but they collide with the inflow surface in such a way that they will be killed by the impact.

For a preferred embodiment of this method, the actual population of insects on a predetermined area is determined due to the quality value of the predetermined area. The following table shows a preferred classification of areas outside buildings, which are awarded for various stages of the quality values. The indicated values are the weight of the population of insects living on one square meter in the vegetation within a year.

For a preferred embodiment of the method, the actual population of insects on a predetermined area is detected by using at least one sensor. Here, a sensor may be provided which determines the insects directly itself. This especially makes sense when the actual population of insects of a particular species of insects has to be determined. However, it is—depending on the biological contexts—also possible by determining the actual population of insects of a particular species of insects to determine the actual population of insects of another, especially related and/or the same habitat preferring insect or to the entire actual population of insects of the area.

A preferred embodiment of a suitable sensor determines, for example, the amount of ants, which are moving in the measurement area, or it determines the population of ants in the area based on the number and size of detected anthills.

For a further preferred embodiment of the method, the parameters are preferably determined by sensors. Therefore, the quality value of the predetermined area can be determined based on the determined parameters and the actual population of insects in that area can be determined. A suitable sensor preferably comprises imaging detection means. As parameters, based on which the quality value is determined, are in particular suitable: the vegetation, the moisture of the soil and/or the moisture of the vegetation, the oxygen content and/or the pollution of the air, the average temperature, the average solar radiation, the average wind

| Quality value stage 0 | Quality value stage II | Quality value stage II | Quality value stage III | Quality value stage IV | Quality value stage V |
|---|---|---|---|---|---|
| Without significance | Minimal significance | Low significance | Average significance | High significance | Very high significance |
| <800 mg/m$^2$ | 800 to 2,000 mg/m$^2$ | 2,000 to 4,000 mg/m$^2$ | 4,000 to 8,000 mg/m$^2$ | 8,000 to 12,000 mg/m$^2$ | >12,000 mg/m$^2$ |
| Bituminized surface | Compost heap | Insect hotel | Single tree | Dry stone wall, stone baskets | Little waters |
| Tiled roof | | Nesting box | Façade greening | Heap of stones, heap of branches | Brooks opening |
| Bitumen sealed terrace Cobbled surface | | | | Hedge, bosk Ruderal area Extensive terrace Fruit orchard | |

In particular, with an increasing stages of the quality value, a higher species diversity has to be assumed and thus a higher weight fraction of the insect species, which have a high value to their ecosystem.

If for the method according to the present invention, the population of insect in the soil should be supported, so it have to be considered the deviating weights of soil-dwelling insects and optionally the deviating weights of a certain insect species or of a certain arthropod species, in particular their quality value in the ecosystem.

Preferably, by the stages of the quality values, the quality value of an area is determined simply and quickly. For determining the quality value of an existing area, the area is preferably classified into a stage of the quality values. On the other hand, starting from the properties of an area with a previously known quality value, it is possible to determine the measures for adjusting the area, which are required for upgrading the area to a desired quality value. However, it should be borne in mind that the actual population of insects of an area also differs significantly depending on the particular climatic conditions, the properties of the soil and the use of land for part of the specified values in the general tables, so that for this purpose, preferably a suitable table is selected.

speed, the color of the vegetation, the properties of the soil, or the presence of bio structures such as stretches of water or heaps of stones. Also, the amount and/or conditions in the presence of different insect species with different ecological values can be used as parameters for determining the quality value of the predetermined area. On the one hand, by using one or more of these parameters, a classification of the area can be determined, and on the other hand, a possible change in the actual population of insects can be determined in dependency on the time.

Starting from the actual population of insects on the predetermined area, the target insect population of this area is determined by the difference of the population of insects, which results from the action of a predetermined amount of product units, using a suitable determination method, which preferably also takes into account the correction factors.

For a preferred embodiment of the method, the required quality value of the predetermined area is determined based on the target population of insects. Also a classification system is preferably used for this purpose, which has been determined in the determination of the actual population of insects due to the quality value of the present area, and which preferably includes the population of insects on an area of a classified quality value stage. By using such a classification system, the required quality value of the predetermined area for providing a livelihood for the target population of insects can be determined quickly and easily.

For a preferred embodiment of the method, the potential of an area is determined by the difference of the product of the quality value of the area and of the subsequent population of insects living in the final state and by the product of the quality value of the area and the subsequent population of insects living in the original status. The potential is preferably adjusted by correction factors to other influencing factors. For example, a factor can be determined, which is directly proportional to the size of the area. Such a factor is preferably selected from the quotient of the size of the difference of the population of insects, and the potential of the area.

For another preferred embodiment of the method, the necessary measures for compensation are determined. This is effected in that by the actual population of insects is divided by the product of the target population of insects and the difference of the population of insects. The calculated factor represents a value for the required adjustment of the biological properties of the area.

For a further preferred embodiment of the method, for determining the target population of insects by the actual population of insects on the predetermined area and the determined difference of the population of insects, a correction by one or more factors is provided. Preferably, the factors are used, by which in particular a time shift between the application of the product unit and the adaptation of the biological properties of the predetermined area is taken into account. Another preferred factor takes into account the effect of the time deployment of the adaptation, meaning an additional correction of the time until when the compensatory habitat unfolds about its intended environmental impact (biodiversity, stabilizing vegetation). Another correction factor preferably takes into account the positive effect of the structural diversity of the biological properties of the predetermined area after the adjustment.

The structural diversity is increased in particular by the introduction of bio structures in the area such as mounds, heaps of stones, heaps of branches, dry stone walls, stone baskets, small stretches of water, plantings such as trees and shrubs in particular, façade greening, insects hotels and openings of brooks. By this, the temporal development of these effects in the area particularly improves the livelihoods of the population of insects and the biodiversity and the quantity of insects in the predetermined area of the habitat is increased. At the same time, the quality value of the predetermined area is increased by the introduction of bio structures, so that the area is suitable as a livelihood for a larger population of insects.

In particular, if the considered populations of insects are insects whose livelihood is related to the properties of the soil, the quality value of the predetermined area can be increased by amending the properties of the soil and by such an adjustment of the biological properties of the area, the settling of the target population of insects can be effected.

Furthermore, an apparatus for the use at the performing of the method for supporting the preservation of the population of insects is proposed. This apparatus comprises an effect detecting means for detecting the lethal effect of a product unit on the population of insects, which preferably derives from at least one detected value the lethal effect of the product unit. Furthermore, the apparatus comprises a quantity detecting means for detecting the amount of product units under consideration, and a determination means for determining the difference of the population of insects resulting from the application of the quantity of the product units.

The apparatus according to the present invention further includes at least one actual detecting means for detecting the actual population of insects on a predetermined area. Into a computing device of the apparatus, values can be read into from the further devices of the apparatus. Said computing device derives the target population of insects on the predetermined area from at least from the values of the difference of population of insects and of the actual population of insects on the predetermined area.

The effect detecting means of the apparatus for the use in performing the method serves for detecting the lethal effect of a product unit on the population of insects. Thereby, the lethal effect of a product unit is preferably referred to the live weight of insects, which are on average killed by the product unit. Depending on the embodiment of the apparatus, the effect detecting means for detecting the lethal effect may be an input device like a keyboard or a touch screen, into which can be read into an existing value representing the lethal effect of the product unit. The effect detecting means may be also a measurement device, by which the active ingredients, and preferably the amount of the active ingredient of a product are detected and the lethal effect of the product unit is derived, preferably in conjunction with the stored data and preferably other information, in particular the information relating to the effect or the use of the product. A value, which has been determined by the effect detecting means for the lethal effect of a product unit, is preferably provided there for the computing device as readable.

The apparatus further comprises a detecting means for detecting the amount of the product units considered. Depending on the embodiment of the apparatus, it can be in particular an input means such as a keyboard or a touch screen, by which a value for the amount of the product units can be entered in or read into the apparatus.

The apparatus further comprises a determining means, which is used to determine the difference of the population of insects resulting from the use of the quantity of the product units. Determining of the difference of the population of insects is carried out, by using the value for the lethal effect of the product unit. Preferably, for this determination, stored data for the killing of insects by the product unit is used in said determining means, such as in particular the weight of the insect or the population density of the insect or its reproduction characteristic.

The apparatus according to the present invention further includes at least one actual detecting means for detecting the actual population of insects on a predetermined area. Besides input devices such as a keyboard or a touch screen, by which a particular value for the quality value of the predetermined area can be read into or can be put into, from which by using stored data the actual population of insects is determined, the apparatus may also preferably comprises immediate actual detection means such as sensors.

As already described in connection with the method for supporting the preservation of the population of insects, a sensor is preferably provided which detects the insects directly itself. For a preferred embodiment, the actual detection means is configured such that due to the detected data, which relates to the actual population of insects of a specific insect, it can be determined the population of insects of another species of insect or the population of insects of the entire actual area.

For a further preferred embodiment of the apparatus, the actual detection means comprises one or more sensors, which detect the parameters that determine the quality value of the predetermined area. Intended in particular in connection with preferably stored in the device data, the actual detection means preferably detects the actual insect population on the predetermined surface. As sensors of such an actual detection means are particularly suitable: humidity sensors, gas and solid-state sensors, temperature sensors, brightness and radiation detection sensors, motion sensors for detecting wind speed, color sensors or cameras preferably with image recognition.

Into the computing device of the apparatus, values from the other devices of the apparatus can be read into. Several elements of the apparatus can thereby be incorporated in one or more functional units of the apparatus. Preferably, in the computing device are arranged the functional units of the effect detecting means, the amount detecting means, the determining means or the actual detecting means. However, these functional units can be arranged locally independently and are preferably at least temporarily connected to each other via radio networks or wired networks.

The computing device determines the target population of insects on the predetermined area from at least the values of the difference of the population of insects and of the actual population of insects. For this purpose, it uses preferably values, which have been at least partly determined by to other devices of the apparatus and in particular it uses computational algorithms as well as data, which have been stored in the computing device.

For a preferred embodiment, in the computing device are also stored measures for adjusting the biological properties of soil. Starting from the detected actual population of insects on a predetermined area the measures are derived, which are suitable for providing a livelihood for the target population of insects on the predetermined area. Preferred measures are in particular the introduction of bio structures in the area or the change of the properties of the soil.

Thus, the apparatus for applying the method for supporting the preservation of the population of insects can determine the necessary compensation for the losses of the insects via the input and/or via the detection of suitable parameters of the application of an insecticidal agent based on its effect on the population of insects. Based on the values of the actual population of insects on a predetermined area, which have been detected by the device, it determined the necessary biological adaptation of the predetermined area for creating a livelihood for the target population of insects.

Further advantages, features and possibilities of the application of the present invention will become apparent from the following description in conjunction with the figures.

Figure 2:
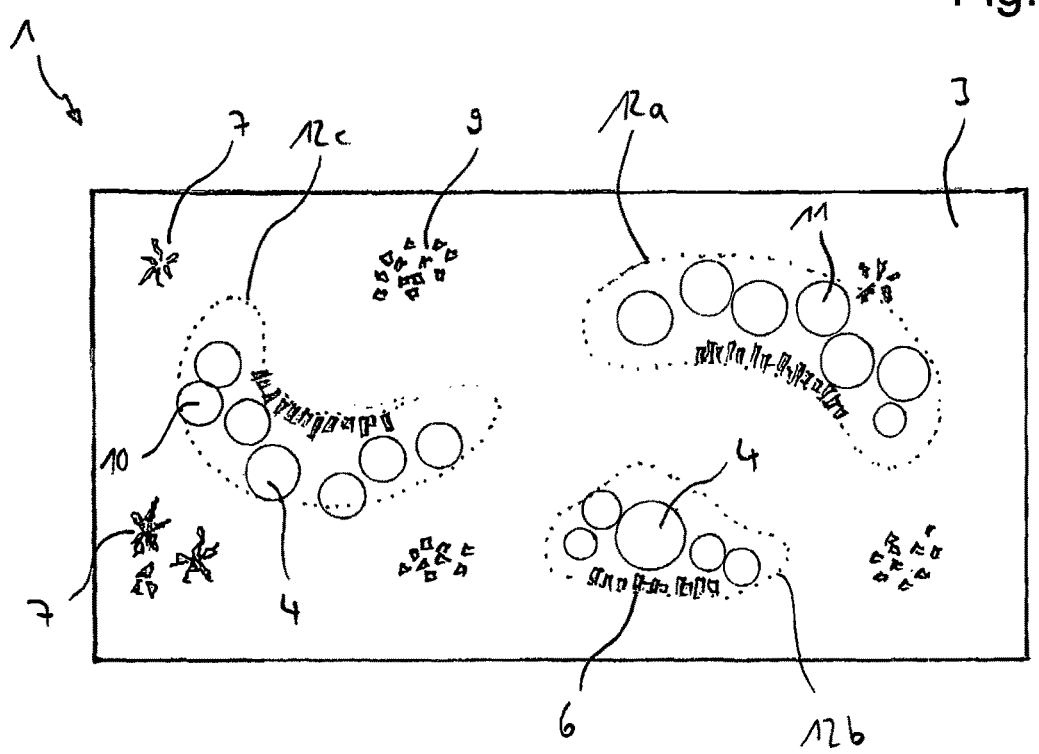
Figure 3:
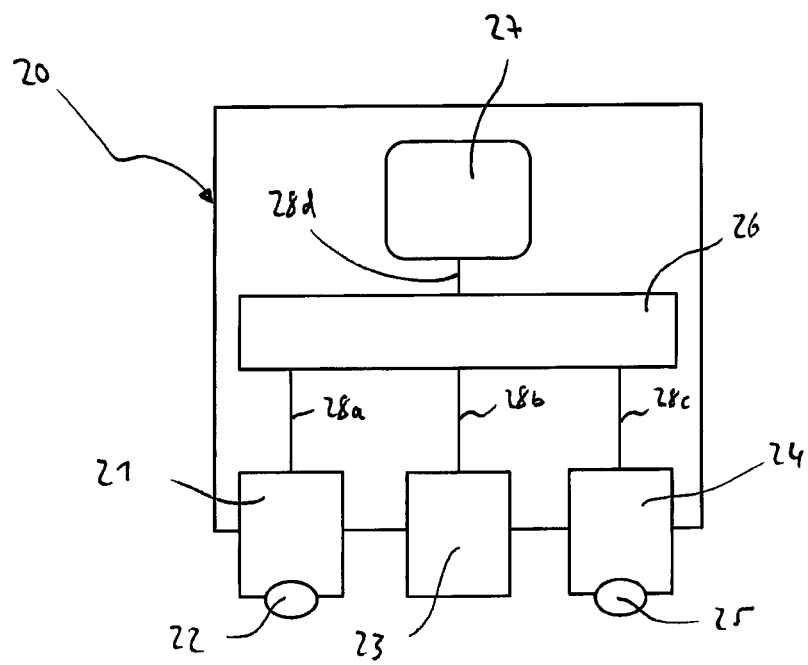
Figure 4:
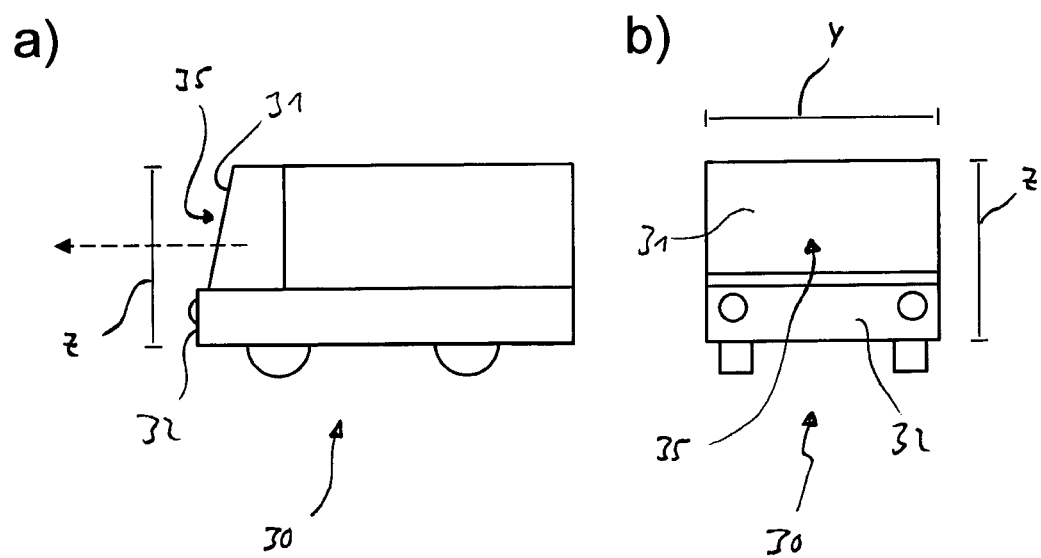

It shows, partially schematically:

FIG. 1: An example of the predetermined area constructed as a flat roof before and after the performing of the method for supporting the conservation of a population of insects, respectively, in a perspective view;

FIG. 2: An example of the predetermined area constructed as a flat roof before and after the performing of the method for supporting the conservation of a population of insects, respectively, in a top view;

FIG. 3: An exemplary apparatus according the present invention for use of a method for supporting the preservation of the population of insects in a schematic view; and FIG. 4: A product unit being exemplary formed as a motor vehicle, on which the method of the invention can be applied to in a side view (FIG. 4a) and in a front view (FIG. 4b).

FIG. 1 shows an example of a predetermined area 2, 3 configured as a flat roof 1, 1' before and after carrying out the method according to the present invention for supporting the preservation of the population of insects, respectively in a perspective view.

The flat roof 1, 1' is determined in the framework of the performing the method according to the present invention as a predetermined area 2 for the supporting of the conservation of a population of insects.

For how many insects the flat roof 1' can essentially provide a habitat in the volume over its area 2, and thus the quality value of the area 2 as a habitat for insects depends on the characteristics of the different parameters, such as the properties of the soil, the vegetation, the presence of bio structures, the humidity, the oxygen content and/or the pollution of the air, the temperature, the sunlight and/or the wind speed.

For the present example, the area 2 of the flat roof 1' is sealed by a tar membrane or bitumen before carrying out the method according to the present invention and it has no other structures, for example bio structures on it. Therefore, the area 2 as a habitat for insects has a very low quality value, which is approximately equal to zero in this example.

For the example described here, the lethal effect of 50,000 units of a mechanical insect control product is compensated to 100%.

This compensation is done by a step of the method according to the present invention by creating a better livelihood for a target population of insects on the flat roof 1' by adjusting the corresponding quality value of the predetermined area 2.

By creating this livelihood, the area is 2 transformed into an altered surface 3 of the then greened flat roof 1, which has a higher quality value as a habitat for insects, compared to the area 2 and thus can accommodate a greater number and density of insects, respectively.

As shown in FIG. 1, the vertical arrow marks a time shift between an instant in time prior to the application of the proposed method and an instant in time after the application of the proposed method.

If, as in the present case, the size of the surface 2 or 3 (in this case 125 m$^2$) is predetermined, it is determined on the basis of the determined values of the lethal effect of the considered product units and on the basis of the insects having a habitat on the area 2 (here approximately zero) which average quality value the area 3 of a greened flat roof 1 should have or how much the quality value by the transformation of the surface 2 should be improved in the area 3, in order to have a livelihood for the desired target population of insects.

For a further embodiment of the application example, however, the target quality value of the predetermined area 3 is defined, based on which then it is calculated the necessary size of the predetermined area 3.

For determining the required quality value of the predetermined area in the embodiment, the correction factors are included, which take into account the conversion time of the surface enhancement in terms of the insect losses and the effect of the development of the effects improving of the area. Also, for the determination of the quality value of the area, a correction factor is set which takes into account the additional structures on the area.

For the present embodiment, the quality value of the area 3 in respect to the quality value of the area 2 is at first improved by applying on the sealed surface of the surface 2 a 10 to 12 cm thick layer of a mineral roof garden substrate or a natural soil, which among other things serves as a basis for the introduction of further bio structures, which improve the quality value of the area 3.

Depending on the influencing environmental parameters such as a solar and wind exposure and/or the possibility of irrigation, the area 3 is intentionally provided with other bio structures until their combination, the composition, the positioning and the quantity in connection with the introduced properties of the soil allows the quality value of the habitat of area 3 corresponding to the desired degree of supporting the reservation of the population of insects.

For this embodiment, as bio structures are used among others plant structures such as bushes 4, shrubs 11 and/or flowering plants 10, which can serve the insects as a food source and/or nesting. In addition, on the roof garden substrate or the natural soil can be incorporated different grasses 8 and other foliage plants.

Even dead plant materials such as tree stumps and/or tree roots 7 and/or round timber sections 6 can improve the habitat for various insects regarding food, hiding places and/or nesting sites and are used herein. Larger mineral structures 5, especially porous stones form hiding places for insects as well as landfills of smaller pebbles 9.

By using the bio structures 4 to 11 on the predetermined area 3, the relative proportion of ecologically valuable species of insects can be increased, which in turn may result in an increase in biodiversity and thus in an increase of the quality value of the predetermined area 3.

FIG. 2 shows an example of a predetermined area 3, which has been formed as a flat roof 1, after carrying out the method according to the present invention for supporting the preservation of the population of insects in the top view.

For this embodiment, in turn, different bio structures are applied to a substrate of the area 3, of which the properties of the soil are characterized by a mineral roof garden substrate or a natural soil, respectively.

The use of the bio structures in this embodiment differs from the embodiment described in the FIG. 1 in the combination, the composition, the positioning and/or the quantity of each bio structure.

Separate planting groups 12a, 12b, 12c comprise, partially enclosed by round timber sections 6, clusters of bushes 4, shrubs 11 and/or flowering plants 10. For this embodiment, also a contribution of trees for the planting can be provided for the flat roofs 1, which have a sufficiently stable construction.

FIG. 3 shows an exemplary apparatus 20 according to the present invention for use in the embodiment of the method for supporting the preservation of the population of insects in a sectional view. The apparatus 20 comprises inter alia an effect detecting means 21, a quantity detecting means 23, a determining means, an actual detecting means 24, and a computing device 26.

The computing device 26 is connected in respect to electrical energy and in respect to one sided and/or both sides signal transmission with all the above mentioned detection means 21, 23, 24, 26 as well as with at least one input means 27 such as a keyboard or touch screen, respectively.

The effect detecting means 21 detects the lethal effect of a product unit on the population of insects, and derives the lethal effect of a product unit from at least one detected value. This detection can be done, for example, by an input means 27 being handled by an expert, or, for example, even by a sensor-based measurement means 22. The measuring means 22 detects the measured values in respect to the presence and/or concentration of certain substances of product units. In connection with the data, which has been stored in the effect detecting means, and other information concerning the application or the use of the product, it is derived the lethal effect of the product unit.

The quantity detecting means 23 detects the amount of the actual product units. For example, this detection can be performed by means of an input means 27 being handled by an expert.

For this embodiment, the determining means is not separately shown and it is part of the computing device 26 and it determines the difference of the population of insects resulting from the application of the quantity of the product units using the determined value for the lethal effect of a product unit and of the stored data, for example in the weight and/or in the reproduction characteristics of certain insects.

The actual detecting means 24 detects the actual population of insects on a predetermined area. This detection can, for example, be performed by means of an input means 27 being handled by an expert. The detection can also be done via the sensor device 25, which itself captures the insects directly or collect directly or indirectly by means of the detection of the actual population of insects of a particular species of insect or the actual population of insects of another insect species or the total actual population of insects of the area 2.

The sensor device 25 of this application example is provided with, for example, at least one sensor as a humidity sensor, a gas and solid state sensor, temperature sensors, light sensors, movement sensor for detecting the wind speed, a color sensor and/or a camera having image recognition.

Into the computing device 26, values can be read from the further devices 21, 23, 24, 26, 27 of the apparatus. From the values for the difference of the population of insects and the actual population of insects on the predetermined area 2, it is determined the target population of insects on the predetermined area 3.

For the embodiment described here, in the computing device 26, measures for the adaptation of biological properties of the soil are stored. Starting from the detected actual population of insects on the predetermined area 2, in particular from the stored measures, suitable measures for providing a livelihood for the target insect population on the predetermined surface 3 are derived.

FIG. 4 shows in a side view (FIG. 4a) and a front view (FIG. 4b) an exemplary product unit, which has been formed as motor vehicle 30, and which can be applied to the method of the present invention.

The motor vehicle 30 is moving at a speed of 100 km/h in the direction of 4a plotted in the FIG. 4a as dashed arrow.

For this case, a flow against surface 35, which in this embodiment is substantially calculated as a product of the width Y and the height Z, is flown against by the relative wind, which results from the running speed of the vehicle 30.

When now flies in the area through which the motor vehicle 30 and thus the flow against surface 35 moves, parts of the insect population of the insects and/or the other arthropods will be killed as soon as they collide particularly with the windshield 31 or the condenser 32 of the vehicle 30. Thus, the motor vehicle 30 has a lethal effect on the population of insects.

The lethal effect of the motor vehicle 30 on the population of insects with an annual mileage of 16,000 km is 28 g of insects in one year. The difference of the population of insects due to the effect of the motor vehicle 30 is therefore 28 g of insects.

The flat roof 1' shown in the FIG. 1 has an area 2, which is sealed by a tar membrane or bitumen and it has no bio structures, which serve as the livelihood of insects. The actual population of insects on the area 2 is therefore determined being approximately zero. The object is that the area 3 of the flat roof 1 also serves for one year as a livelihood for the difference of the population of insects which will be killed due to the effect of the motor vehicle 30. For the simple calculation method used in this embodiment, the target population of insects on the area 3 corresponds to the difference of the population of insects, as the actual population of insects is approximately zero on the area 2.

For a further step of the embodiment for the application of the proposed method, it is provided a surface 3, which provides a livelihood corresponding to the target population of insects of 28 g of insects in one year, by adjusting the biological properties of the area 2, by providing a suitable soil structure and by the introduction of plantings as bushes 4 and bushes 11. After the implementation of these measures, the motor vehicle 30 is provided with a corresponding marking, wherein for the lethal effect of this motor vehicle on the population of insects the conservation measure has been carried out.

The invention claimed is:

1. A method for supporting the preservation of insects comprising the steps of:
   determining the lethal effect of one product unit on a first population of insects,
   determining the difference, as a positive amount, in the first population of insects due to the effect of a certain amount of product units,
   determining a second population of insects, namely an actual population of insects in a predetermined area by using at least one sensor which detects at least one parameter, due to which the biological properties of the predetermined area, also referred to as the quality value of the predetermined area, are determined based on which the actual insect population in the area can be determined, wherein the parameter is selected from a group, which comprises: the vegetation, the humidity, the oxygen content and/or the air pollution, the temperature, the solar radiation, the wind speed, the color, the conditions of the soil and the presence of bio structures, such as mounds, heaps of stones, heaps of branches, dry stone walls, stone baskets, small stretches of water, plants, insect hotels and opening of brooks,
   determining a target population of insects in the predetermined area, the target population of insects being the sum of the actual population of insects in the predetermined area and the difference in the first population of insects, which difference in the population of insects is optionally increased or decreased by a factor, and
   providing a livelihood for the target population of insects in the predetermined area by increasing the quality value of the area by introducing bio structures in the area.

2. The method for supporting the preservation of insects according to claim 1, characterized in that the lethal effect of the product unit on the first population of insects is a mechanical effect and/or a chemical effect.

3. The method for supporting the preservation of insects of claim 1, characterized in that the difference in the population of insects is increased or decreased by a factor which takes into account the time delay between the application of the certain amount of product units and the adaptation of the biological properties of the predetermined area, and/or the development of the effects of the adjustment and/or the effect of the structural diversity of the biological properties.

4. The method for supporting the preservation of insects according to claim 1, characterized in that the quality value of the predetermined area is increased by introducing bio structures in the area.

5. The method for supporting the preservation of insects according to claim 4, characterized in that the bio structures, which have been introduced in the area, are selected from a group comprising: mounds, heaps of stones, heaps of branches, dry stone walls, stone baskets, small stretches of water, plants as particular trees and shrubs, facade greening, insects hotels and openings of brooks.

6. The method for supporting the preservation of insects according to claim 1, characterized in that the quality value of the predetermined area is increased by changing the properties of the soil.

7. The method for supporting the preservation of insects according to claim 1, characterized in that it further comprises the step of marking a further product unit, which marking indicates that the method was performed to compensate for its lethal effect.

8. An apparatus for applying a method for supporting the preservation of insects comprising:
   a means for:
      a. detecting the lethal effect of one product unit on a first population of insects, the lethal effect of one product unit being preferably derived from at least one detected value,
      b. detecting the number of the product units which have been considered,
      c. determining the difference in the first population of insects resulting from the application of the number of the product units, and
   at least one means for detecting a second population of insects, namely an actual population of insects in a predetermined area, wherein the means for detecting a second population of insects comprises at least one sensor, which detects at least one parameter, due to which the biological properties of the predetermined area, also referred to as the quality value of the predetermined area, are determined based on which the actual population of insects in the predetermined area can be determined, wherein the parameter is selected from a group, which comprises: the vegetation, the humidity, the oxygen content and/or the air pollution, the temperature, the solar radiation, the wind speed, the color, the conditions of the soil and the presence of bio structures, such as mounds, heaps of stones, heaps of branches, dry stone walls, stone baskets, small stretches of water, plants, insect hotels and opening of brooks and
   a computing device, into which the values from the means for detecting the lethal effect of one product unit on a first population of insects, the means for detecting the number of the product units which have been considered, the means for determining the difference in the first population of insects resulting from the application of the number of the product units, and the at least one means for detecting an actual population of insects in a predetermined area of the apparatus can be read into and which at least determines a target population of insects in the predetermined area based on the values for the difference in the first population of insects and the actual population of insects in the predetermined area.

9. The apparatus for applying a method for supporting the preservation of insects according to claim 8, wherein measures for adjusting the biological properties of the soil are stored in the computing device and wherein these measures are derived on the basis of the detected actual population of insects in the predetermined area for providing a livelihood for the target insect population in the predetermined area.

\* \* \* \* \*